(12) United States Patent
Jaremo et al.

(10) Patent No.: US 6,288,778 B1
(45) Date of Patent: Sep. 11, 2001

(54) HANDLING OF BLOOD IN BAGS BY MEANS OF ROTATING DISCS

(75) Inventors: Petter Jaremo, Norrkoping; Per Hvass, Tullinge, both of (SE)

(73) Assignee: Gematron Medical AB, Skarholmen (SE)

( * ) Notice: Subject to any disclaimer, the term of this patent is extended or adjusted under 35 U.S.C. 154(b) by 0 days.

(21) Appl. No.: 09/509,568

(22) PCT Filed: Oct. 15, 1998

(86) PCT No.: PCT/SE98/02061
§ 371 Date: May 18, 2000
§ 102(e) Date: May 18, 2000

(87) PCT Pub. No.: WO99/26066
PCT Pub. Date: May 27, 1999

(30) Foreign Application Priority Data

Nov. 18, 1997 (SE) .................................................. 9704213

(51) Int. Cl.[7] .................................................. G01N 33/48
(52) U.S. Cl. .................................................. 356/39; 422/65
(58) Field of Search .................................................. 356/39, 40, 41; 364/497, 500, 506, 525

(56) References Cited

U.S. PATENT DOCUMENTS

| | | | |
|---|---|---|---|
| 4,125,828 | * 11/1978 | Resnick et al. | 340/146.3 CA |
| 4,250,266 | * 2/1981 | Wade | 435/289 |
| 5,345,395 | * 9/1994 | Griner | 364/497 |
| 5,551,941 | * 9/1996 | Howell | 494/16 |
| 5,723,050 | * 3/1998 | Unger et al. | 210/772 |

* cited by examiner

Primary Examiner—Frank G. Font
Assistant Examiner—Roy M. Punnoose
(74) Attorney, Agent, or Firm—Dennison, Scheiner, Schultz & Wakeman

(57) ABSTRACT

An apparatus for handling blood in bags includes a housing having disposed therein a plurality of generally circular discs arranged one above another, spaced from each other, parallel with each other, and rotatable about a common central axis, with each disc forming an angle of inclination to said central axis, and a device for rotating the discs about the common central axis. Each of the discs has two parallel surfaces with a peripheral portion, and a device for retaining at least one blood bag at the peripheral portion of one surface, said device including an aperture through the disc. The apparatus further includes a light source arranged beneath each of the discs and a light sensitive member arranged above each of the discs, each light source and light sensitive member being disposed such that light being transmitted by the light source passes through the aperture in the disc to impinge on the light sensitive member, thereby measuring glare of thrombocytes in blood in a bag retained on the disc.

8 Claims, 5 Drawing Sheets

HANDLING OF BLOOD IN BAGS BY MEANS OF ROTATING DISCS

BACKGROUND OF THE INVENTION

The present invention relates to a procedure for examining and storing blood in bags. These bags are placed at the periphery of a circular disc. One or more discs may be placed one above the other, the discs inclined and then rotated so that the contents of the bags becomes thoroughly mixed. Each bag is allowed to pass a station, where a ray of light is directed towards a bag from below, the disc being provided with an aperture allowing the ray of light to reach the bag, pass the bag and then be received by a sensor after the ray of light has passed the bag. The light absorbed by the sensor is then conveyed to a computer for analysis.

SUMMARY OF THE INVENTION

The object of the invention is to provide a practical unit that can be placed in any health care center or hospital. The unit is in the nature of a parallel-epipedic cabinet. A number of circular discs are arranged in the cabinet, spaced from each other and parallel with each other. The discs have an axis of rotation that is substantially vertical, and runs through the center of the discs. The discs are caused to rotate by a shaft located parallel with the axis of rotation and situated external to the discs. The shaft external to the discs influences an endless belt, chain or the like and transmits rotation to the discs which are suitably journalled. An attachment means for bags is arranged along the periphery of the discs so that the bags can be arranged radially. The bag is secured at its outer end by a hook arrangement and the inner end of the bag is secured by a spring element which is placed over the front portion of the bag and secured to the disc on both sides of the bag. Beneath each bag, the disc is provided with an aperture so that a ray of light can pass through the disc and through the bag, and above the light-generating unit is a light sensor so that when a disc rotates, bags arranged on the disc will in turn pass said light source. The sensor takes care of the light obtained and supplies it to a computer which analyses the light obtained. The light rays are constant and when they pass the blood it is subjected to glare, this glare being produced by the thrombocytes. It should be noted here that the thrombocytes may assume different shapes and the glare may therefore differ depending on the condition of the thrombocytes.

Each bag should suitably be given a designation. The unit is provided on one side with a number of openable hatches in front of each disc. Using suitable automatic mechanisms, a specific bag containing a specific quality of blood can be ordered to an opening, and when this bag has arrived in front of an opening it is just a question of opening this and withdrawing the bag. It is extremely convenient to have a cabinet of the type described, with a plurality of discs arranged one above the above so that a very large number of bags can be stored on the discs and where the quality of the blood in the various bags can be determined. Thanks to this, an operator can immediately select a specific bag with specific blood quality. The cabinet thus provides a large storage unit for blood bags of different quality and a bag with the desired quality of blood can be obtained quickly and easily.

BRIEF DESCRIPTION OF THE DRAWINGS

The invention will be described in the following with reference to the accompanying drawings, in which.

DESCRIPTION OF THE PREFERRED EMBODIMENTS

Figure 1:
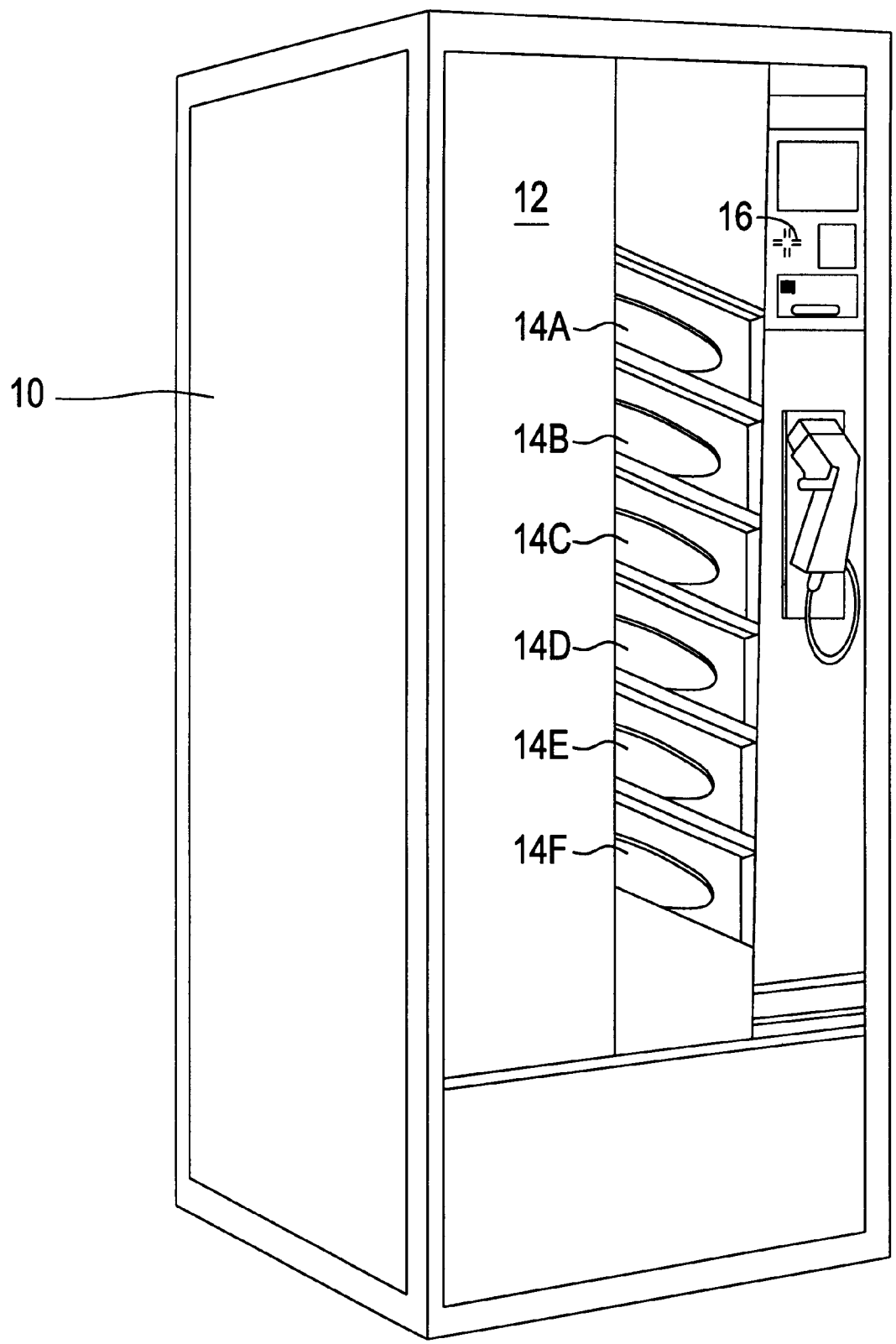
FIG. 1 is a plan view of an apparatus according to the invention.

FIG. 1 shows the unit comprising a parallel-epipedic cabinet 10 in which all the side walls are smooth except for one wall 12 which contains six hatches of glass or plastic 14A–14F which can be opened and closed. Beside these hatches is a control panel 16 by means of which a suitable blood bag can be selected.

Figure 2:
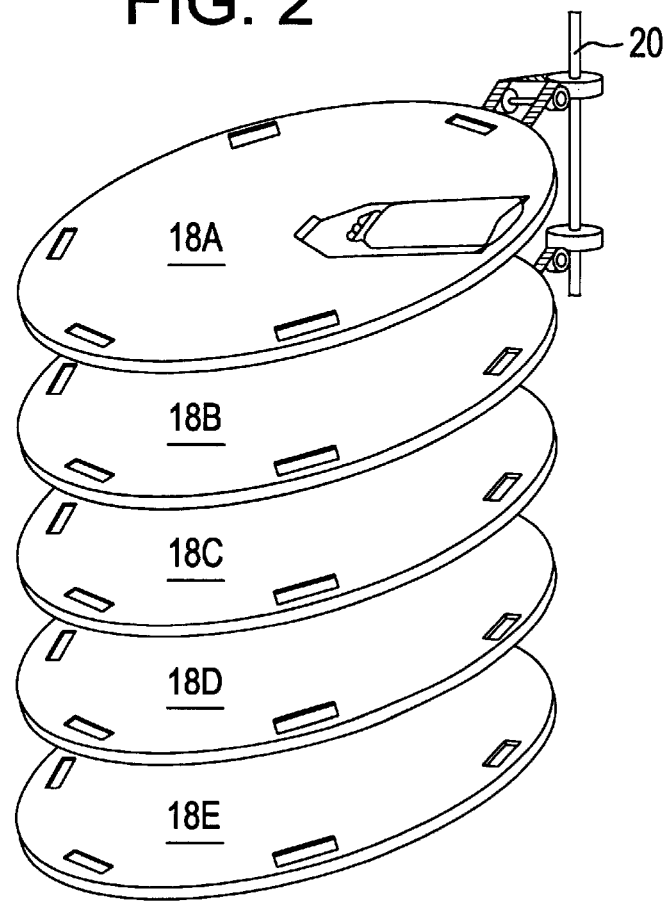
FIG. 2 is a plan view of a plurality of discs according to the invention, including an external rotating shaft, viewed from above.
Figure 3:
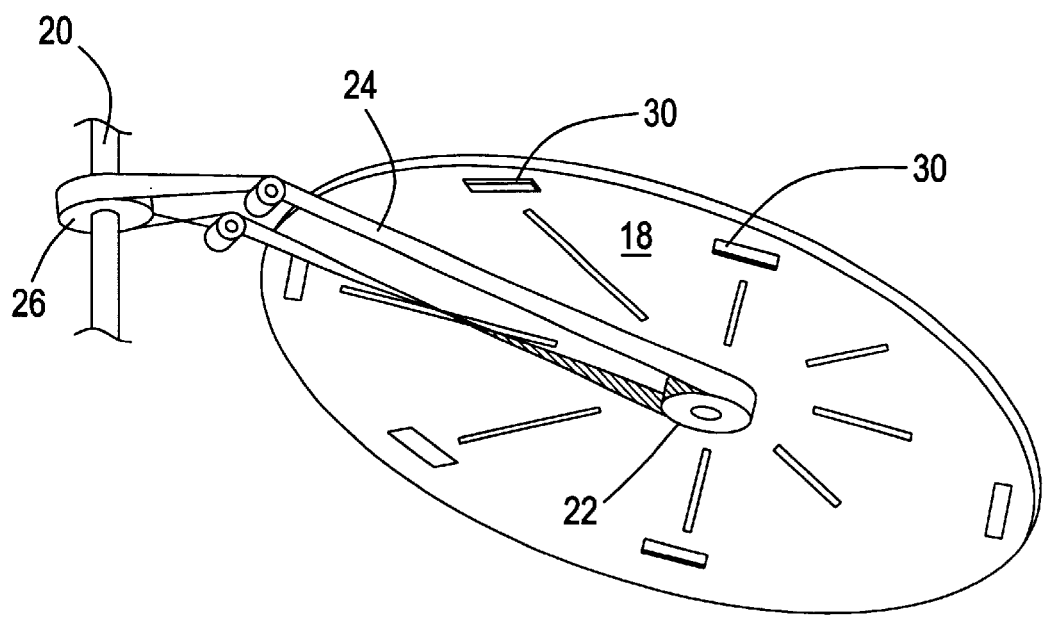
FIG. 3 is a plan view of a disc shown in FIG. 2 viewed from below.
Figure 4:
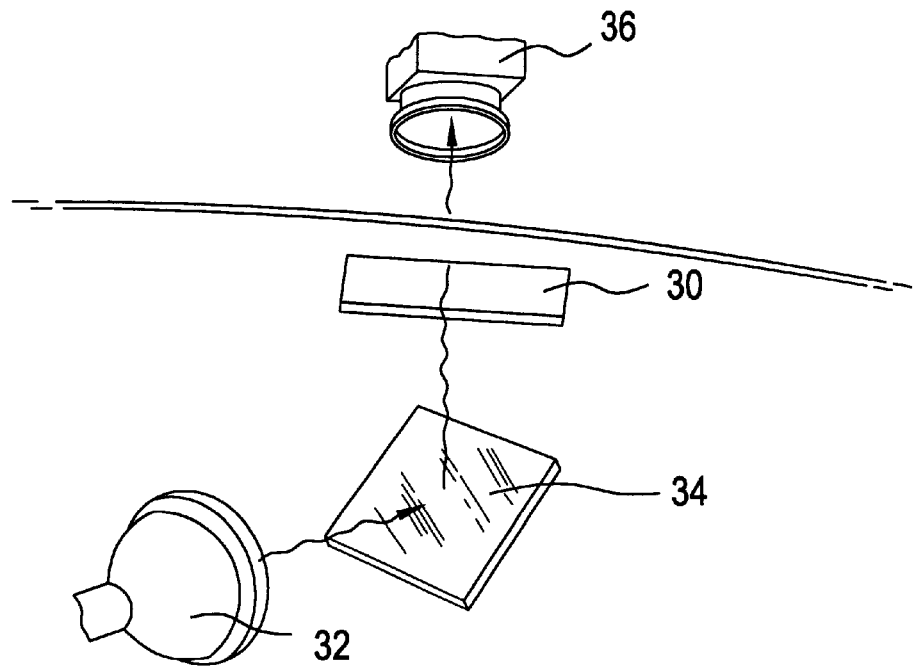
FIG. 4 is a plan view of light transmitting and receiving means viewed from below a disc.
Figure 5:
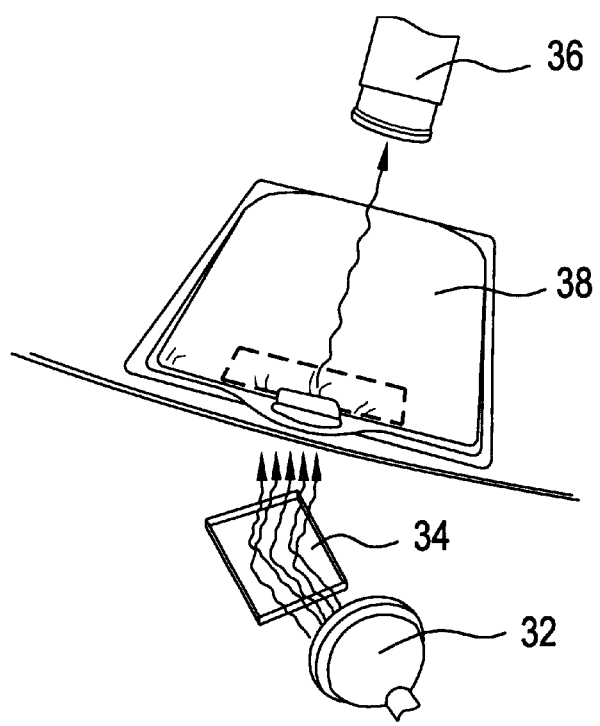
FIG. 5 is a plan view of light transmitting and receiving means viewed from above a disc.

FIG. 2 shows five circular discs 18A–18E journalled pivotably in such a way that they can be caused to rotate without a central shaft. All the discs are inclined and form an angle with the central axis. All the discs are also parallel with each other and situated a predetermined distance from each other. The discs are designed to have bags arranged radially at the periphery and suitably secured. Said discs are driven by a drive shaft 20 located outside the discs. Each disc is driven individually as illustrated in FIG. 3 where it can be seen that each of the circular discs 18 is provided with a corrugated wheel 22 at its center. An endless belt 24 is placed around the wheel 22 and also around a wheel 26 on the drive shaft 20. Drive wheel, driven wheel and belt are also rough in order to avoid friction. FIG. 3 also shows that the circular disc has a plurality of apertures 30 and that such apertures are provided for each bag placed around the periphery of the disc. As shown in FIGS. 4 and 5, for each disc there is a fixed station consisting of a light body 32 with reflector 34 so that light passes through an aperture 30 in a disc when the aperture passes the light point. Above the light point is a sensor 36, the light also passing through blood bag 38.

Figure 6:
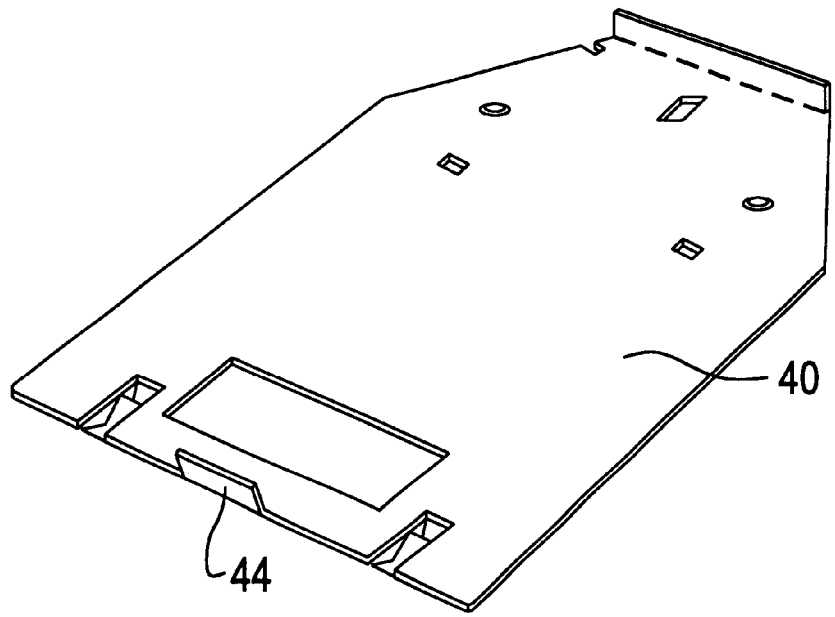
FIG. 6 is a plan view of a retaining means for a blood bag.
Figure 7:
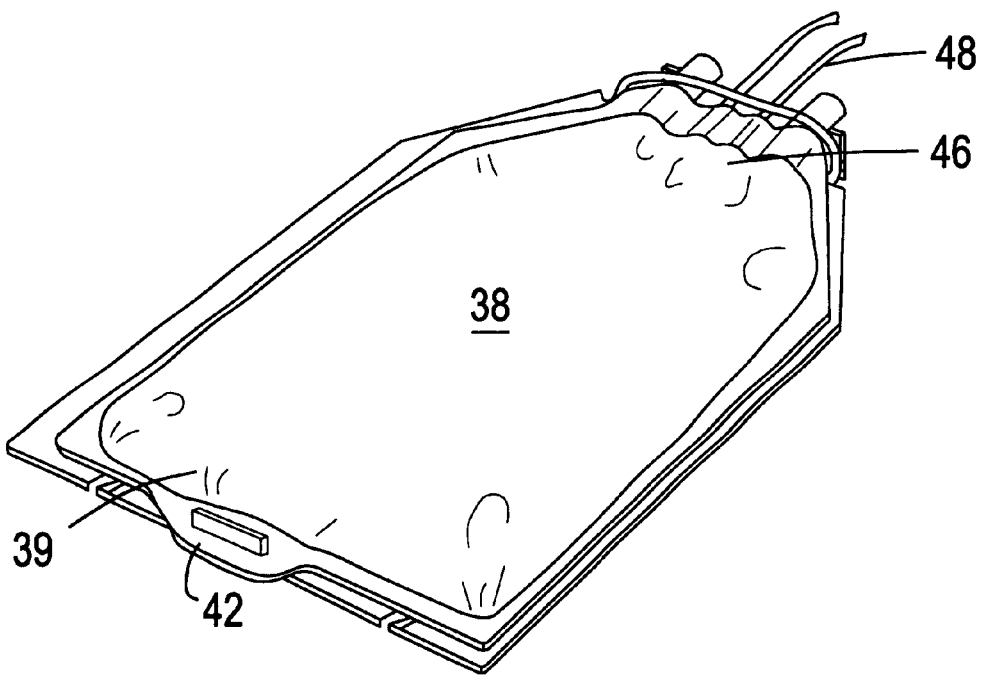
FIG. 7 is a plan view of a blood bag retained on the retaining means of FIG. 6.

FIG. 6 shows a holder 40 for a bag which is disposed on each point of a disc where a bag is to be placed, and FIG. 7 shows clearly how a bag is placed on the holder shown in FIG. 6. For attachment, each bag 38 is provided at its lower end 39 with an eye 42 which is threaded over a protrusion 44 on the holder, and the upper portion of each bag 46 is secured with the aid of an elastic band 48 or the like which is placed over the bag and is attached in the holder itself.

Figure 8:
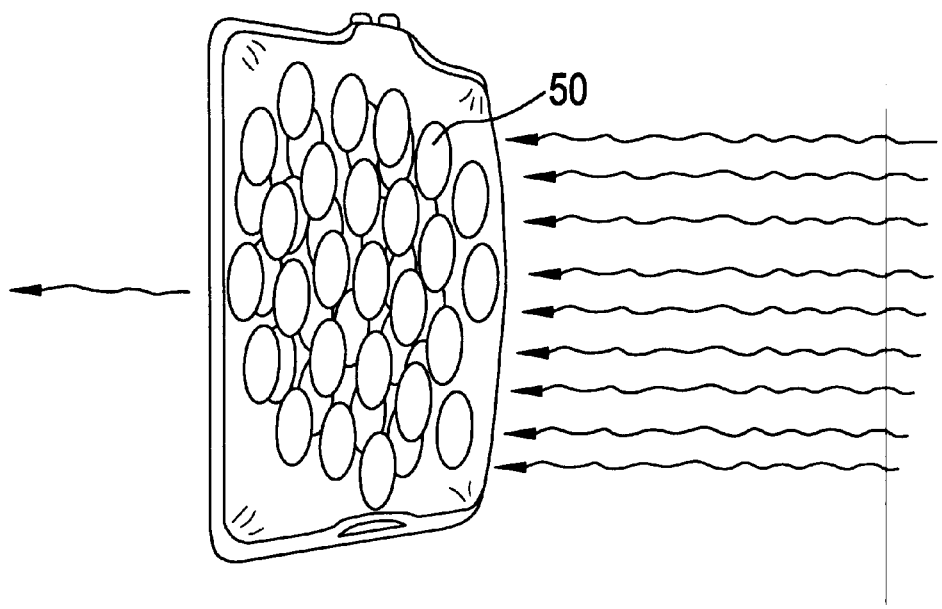
FIGS. 8 and 9 are schematic views of light passing through a blood bags.
Figure 9:
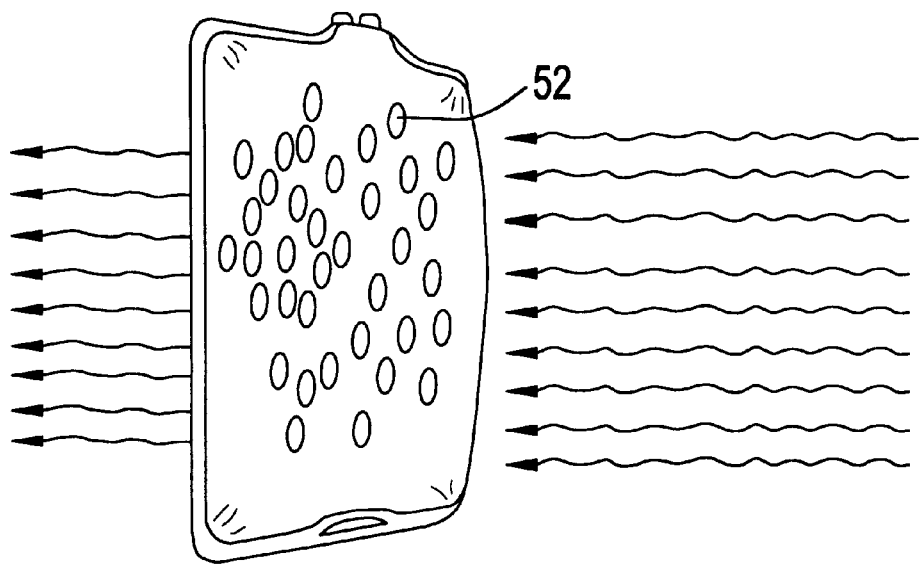

FIGS. 8 and 9 show how illumination of thrombocytes 50 or 52 occurs.

Each of the six circular discs may be provided with a full complement of blood bags, these blood bags being introduced through said six openings in the cabinet. The cabinet can act as storage means for a large number of blood bags and the contents in all the blood bags can be thoroughly mixed upon rotation of the discs. The automatic mechanism with which the cabinet is provided allows a desired blood bag to be conveyed to a hatch where it can be withdrawn. To avoid mistakes the locking devices of the hatches are so constructed that only the hatch containing the desired blood bag can be opened and other hatches remain closed.

What is claimed:

1. An apparatus for handling blood in bags, comprising a housing having disposed therein a plurality of generally circular discs arranged one above another, spaced from each other, parallel with each other, and rotatable about a common central axis, with each disc forming an angle of inclination to said central axis, and means for rotating the discs about the common central axis, each of said discs comprising two parallel surfaces with a peripheral portion, and means for retaining at least one blood bag at the peripheral portion of one said surface, said means comprising an aperture through the disc, said apparatus further comprising a light source and a light sensitive member arranged such that light transmitted by the light source passes through the aperture in the disc to impinge on the light sensitive member, thereby measuring glare of thrombocytes in blood in a bag retained on the disc.

2. Apparatus as in claim 1, wherein the means for rotating comprises a drive shaft disposed externally to the discs, and parallel with the axis of rotation of the discs, and means for transmitting rotary motion from the drive shaft to the discs.

3. Apparatus as in claim 2, wherein the means for transmitting comprises a belt or chain.

4. Apparatus as in claim 1, wherein the housing comprises a closable opening arranged to permit withdrawal of a desired bag.

5. Apparatus as in claim 1, additionally comprising electronic means for storing data relating to a bag retained on a disc.

6. Apparatus as in claim 5, wherein the electronic means comprises means for delivering a desired bag to an opening for removal from the housing.

7. Apparatus as in claim 1, wherein the means for retaining comprises a hook disposed at one end of the means for retaining, and elastic means disposed at an opposite end of the means for retaining.

8. Apparatus as in claim 1, wherein a light source is arranged beneath each said disc, and a light sensitive member is arranged above each said disc.

* * * * *

UNITED STATES PATENT AND TRADEMARK OFFICE
CERTIFICATE OF CORRECTION

PATENT NO. : 6,288,778 B1
DATED : September 11, 2001
INVENTOR(S) : Petter Jaremo et al.

It is certified that error appears in the above-identified patent and that said Letters Patent is hereby corrected as shown below:

<u>Title page,</u>
Change after Item " [22] PCT Filed: " change "October 15, 1998" to
-- November 15, 1998 --.

Signed and Sealed this

Twenty-sixth Day of February, 2002

Attest:

*Attesting Officer*

JAMES E. ROGAN
*Director of the United States Patent and Trademark Office*